United States Patent
Shioda

(10) Patent No.: US 9,936,785 B2
(45) Date of Patent: Apr. 10, 2018

(54) METHOD FOR SUCCESSIVELY PERFORMING HAIR DYEING AND HAIR STRAIGHTENING

(71) Applicant: ICTB GLOBAL CO., LTD., Yokohama-shi, Kanagawa (JP)

(72) Inventor: Masataka Shioda, Yokohama (JP)

(73) Assignee: ICTB GLOBAL CO., LTD., Yokohama-shi (JP)

( * ) Notice: Subject to any disclaimer, the term of this patent is extended or adjusted under 35 U.S.C. 154(b) by 0 days.

(21) Appl. No.: 15/318,299

(22) PCT Filed: Sep. 26, 2014

(86) PCT No.: PCT/JP2014/004926
§ 371 (c)(1),
(2) Date: Dec. 12, 2016

(87) PCT Pub. No.: WO2016/046864
PCT Pub. Date: Mar. 31, 2016

(65) Prior Publication Data
US 2017/0112253 A1   Apr. 27, 2017

(51) Int. Cl.
*A61Q 5/10* (2006.01)
*A45D 7/06* (2006.01)
*A61Q 5/04* (2006.01)
*A61K 8/19* (2006.01)
(Continued)

(52) U.S. Cl.
CPC .............. *A45D 7/06* (2013.01); *A45D 2/001* (2013.01); *A45D 7/02* (2013.01); *A45D 7/04* (2013.01);
(Continued)

(58) Field of Classification Search
CPC . A61Q 5/04; A61Q 5/10; A61Q 5/065; A61Q 5/06; A61K 8/19; A61K 8/22;
(Continued)

(56) References Cited

U.S. PATENT DOCUMENTS 4,781,724 A    11/1988  Wajaroff et al.
2003/0084518 A1  5/2003  Schonert et al.

FOREIGN PATENT DOCUMENTS

EP    2 191 864 A1    6/2010
EP    2 191 865 A1    6/2010
(Continued)

OTHER PUBLICATIONS

English transaltion (Aug. 15, 2017) of the Japanese Patent No. JP 2004217589 A.*

(Continued)

*Primary Examiner* — Eisa B Elhilo
(74) *Attorney, Agent, or Firm* — Oliff PLC

(57) ABSTRACT

A method for successively performing hair dyeing and hair straightening, the method including the steps of: performing dyeing on hair; applying, to the hair immediately after being subjected to dyeing, a reducing first agent containing a basic dye and/or an HC dye, and leaving the hair for a certain time, thereby performing reduction on cystine bonds; shaping the hair that has been subjected to reduction into a straight configuration; and applying an oxidizing second agent to the hair that has been shaped into a straight configuration, and leaving the hair for a certain time, thereby performing oxidation for reforming the cystine bonds.

4 Claims, 2 Drawing Sheets

(51) Int. Cl.
*A61K 8/22* (2006.01)
*A45D 2/00* (2006.01)
*A61K 8/41* (2006.01)
*A61K 8/46* (2006.01)
*A61Q 5/06* (2006.01)
*A45D 7/02* (2006.01)
*A45D 7/04* (2006.01)
*A45D 7/00* (2006.01)

(52) U.S. Cl.
CPC ............... *A45D 7/045* (2013.01); *A61K 8/19* (2013.01); *A61K 8/22* (2013.01); *A61K 8/411* (2013.01); *A61K 8/416* (2013.01); *A61K 8/46* (2013.01); *A61Q 5/04* (2013.01); *A61Q 5/06* (2013.01); *A61Q 5/065* (2013.01); *A61Q 5/10* (2013.01); *A45D 2007/001* (2013.01); *A61K 2800/805* (2013.01)

(58) Field of Classification Search
CPC .......... A61K 8/46; A61K 8/411; A61K 8/416; A61K 2800/805; A45D 7/06; A45D 2007/001; A45D 2/001
See application file for complete search history.

(56) References Cited

FOREIGN PATENT DOCUMENTS

| | | | |
|---|---|---|---|
| JP | S63-501873 A | 7/1988 | |
| JP | 2003-231619 A | 8/2003 | |
| JP | 2003231619 A * | 8/2003 | ............... A61K 7/13 |
| JP | 2003-321332 A | 11/2003 | |
| JP | 2004-217589 A | 8/2004 | |
| JP | 2004217589 A * | 8/2004 | ............... A61K 7/09 |
| JP | 2004-315410 A | 11/2004 | |
| JP | 2006-182685 A | 7/2006 | |

OTHER PUBLICATIONS

English transaltion (Aug. 15, 2017) of the Japanese Patent No. JP 2003231619 A.*
English transaltion (Aug. 15, 2017) of the claims in the Japanese Patent No. JP 2004217589 A.*
Jan. 20, 2015 Search Report issued in International Patent Application No. PCT/2014/004926.

* cited by examiner

METHOD FOR SUCCESSIVELY PERFORMING HAIR DYEING AND HAIR STRAIGHTENING

TECHNICAL FIELD

The present invention relates to a method for performing hair dyeing (hair coloring) and hair straightening in a series of successive steps. More particularly, the present invention relates to a method for successively performing hair dyeing and hair straightening that enables retention of sufficient color development, which has been difficult to achieve by a conventional technique, even when straightening is successively performed immediately after dyeing.

BACKGROUND ART

Hair straightening treatment has hitherto been known as a cosmetic technique for fixing curly or frizzy hair in a substantially straight state. Various small improvements have been made for hair straightening treatment, and they are generally done in the following manner. A reducing first agent of thioglycolic acid or the like serving as a reducing agent for cystine bonds that crosslink the main chains of keratin constituting hair is applied to the hair, and the hair is left for a certain time, thereby to break the cystine bonds, followed by washing with water and drying. By breaking the cystine bonds, the distorted cross-linked structure, which is the cause of curly or frizzy hair, is eliminated. Then, straight ironing is performed on the hair in which the cystine bonds have been broken, thereby shaping the hair into straight hair. Next, an oxidizing second agent containing an oxidizing agent such as hydrogen peroxide or sodium bromate is applied to the hair that has been shaped into straight hair, and the hair is left for a certain time, thereby to reform the cystine bonds, followed by washing with water and drying.

When the above-described reducing first agent is applied to the hair, the cystine bonds are broken to loosen the bonding between keratin molecules, resulting in a problem that the hair coloring dye attached to or charged in a matrix inside the hair is flows out to cause a color loss. For this reason, when hair straightening is successively performed immediately after hair dyeing, the hair coloring dye used for dyeing performed immediately before hair straightening flows out, so that it has not been possible to sufficiently retain the color of the dyed hair after hair straightening. Accordingly, to perform hair dyeing and hair straightening, it has been usually necessary to perform hair dyeing treatment after an interval of at least about one week after hair straightening treatment until the cystine bonds are sufficiently reformed. However, in such a case, a person to be treated needs to take time and trouble to make a visit to a hair salon twice on separate days for receiving hair straightening and hair dyeing. To save such time and trouble, there is a need for a method that enables hair dyeing and hair straightening to be performed by a single visit to a hair salon.

As a technique for solving such a problem, PTL 1 below discloses a method for simultaneously performing hair straightening treatment and hair dyeing treatment, which is a method for successively performing hair straightening treatment and hair dyeing treatment on hair at once by using a hair straightening agent composed of a hair reducing first agent and an oxidizing second agent, the method including a series of successive steps of: treating hair with the first agent into a reduced state; subsequently performing hair dyeing by using a treatment agent containing a basic dye and/or an HC dye; and oxidizing the dyed hair in a reduced state by treating the hair with the second agent.

CITATION LIST

Patent Literature

[PTL 1] Japanese Laid-Open Patent Publication No. 2004-315410

SUMMARY OF INVENTION

Technical Problem

In the method for simultaneously performing hair straightening and hair dyeing disclosed in PTL 1, dyeing is performed with the treatment agent containing a basic dye and/or an HC dye after the step of treating hair with the reducing agent in hair straightening. Thereafter, the dyed hair in the reduced state is treated with the second agent serving as an oxidizing agent so as to be oxidized, thus performing dyeing between the reduction and the oxidation in the hair straightening step. The treatment agent containing a basic dye and/or an HC dye used here is not intended to achieve dyeing, such as permanent dyeing or semi-permanent dyeing, that provides long term color retention, but achieves temporary dyeing, such as the so-called hair manicure, color rinse, or color treatment, that is likely to cause color loss, and thus cannot provide sufficient hair dyeing effect or color retention.

It is an object of the present invention to provide a method for successively performing hair dyeing and hair straightening that enables the color of dyed hair to be sufficiently retained even when hair straightening is performed immediately after dyeing.

Solution to Problem

A method for successively performing hair dyeing and hair straightening according to the present invention includes the steps of: performing dyeing on hair; applying, to the hair immediately after being subjected to dyeing, a reducing first agent containing a basic dye and/or an HC dye, and leaving the hair for a certain time, thereby performing reduction on cystine bonds; shaping the hair that has been subjected to reduction into a straight configuration; and applying an oxidizing second agent to the hair that has been shaped into a straight configuration, and leaving the hair for a certain time, thereby performing oxidation for reforming the cystine bonds. With this method for successively performing hair dyeing and hair straightening, in the reduction step in hair straightening treatment, it is possible to inhibit the outflow of the hair coloring dye applied to the hair during dyeing that has been performed immediately before the reduction step, and to compensate for decolorization of the hair coloring dye. Such a method enables hair straightening to be successively performed after hair dyeing, and therefore, a person to be treated can finish hair dyeing and hair straightening by a single treatment by making only a single visit to a hair salon where the person receives the treatments. Note that "immediately after being subjected to dyeing" means that hair straightening treatment is performed within the same day after dyeing.

It is preferable that the step of performing dyeing is a step of performing dyeing by using a two-agent type hair coloring agent prepared by mixing a dyeing first agent with a dyeing second agent, the dyeing first agent includes an oxidation dye and an alkaline agent, and the dyeing second agent includes a hydrogen peroxide solution. Conventionally, two-agent type hair coloring agents prepared by mixing a dyeing first agent containing a p-phenylenediamine-type or an aminophenol-type oxidation dye and an alkaline agent with a dyeing second agent containing a hydrogen peroxide solution as a main component have been widely used due to their excellent color retention. When such a two-agent type hair coloring agent is applied to hair, the oxidation dye that has penetrated into the hair is oxidatively polymerized in the hair, thereby to produce an indo-dye, which is bulky and thus is not easily removed from the hair. The indo-dye provides excellent color retention of the dyed hair and can achieve a wide variety of color tones. However, when hair straightening treatment is performed immediately after such dyeing, the cuticle on the hair surface is loosened by the swelling of the hair as a result of the cystine bonds being broken, so that the non-polymerized, low-molecular weight oxidation dye flows to the outside of the hair. By including an HC dye and/or a basic dye in the reducing first agent, the HC dye and/or the basic dye fills gaps in the cuticle, thus preventing the outflow of the oxidation dye and compensating for the color of the hair. Accordingly, it is possible to sufficiently retain the color of the dyed hair even when hair straightening is performed immediately after dyeing.

It is preferable that the step of performing dyeing is a step of performing dyeing by using a two-agent type hair coloring agent prepared by mixing a dyeing first agent with a dyeing second agent, and it is preferable to use a two-agent type hair coloring agent in which the dyeing first agent includes a basic dye and/or an HC dye and an alkaline agent, and the dyeing second agent includes a hydrogen peroxide solution. The above-described oxidation dye serving as the hair coloring dye is known to cause a skin disorder. The basic dye and/or the HC dye is known to be safer than the oxidation dye, but is disadvantageous in that it is difficult to be fixed into the hair structure and thus tends to be washed out. Therefore, in general, basic dyes and HC dyes have been used, for example, for hair manicure that lasts only for about one to two weeks, as well as color rinse and color treatment that continue to provide color by being used several times a week. By mixing such a basic dye or an HC dye with an alkaline agent to prepare a first agent, and using the first agent in combination with a second agent containing a hydrogen peroxide solution, it is possible to achieve hair dyeing with excellent color retention without using any oxidation dye. However, when hair straightening treatment is performed immediately after such hair dyeing, the cuticle on the hair surface is loosened by the swelling of the hair as a result of the cystine bonds being broken, so that the basic dye and/or the HC dye flows to the outside of the hair. By including an HC dye and/or a basic dye in the reducing first agent, the HC dye and/or the basic dye fills gaps in the cuticle, thus preventing the outflow of the basic dye and/or the HC dye applied by dyeing and compensating the color of the hair. Accordingly, it is possible to sufficiently retain the color of dyed hair even when hair straightening is performed immediately after hair dyeing.

It is preferable that a total ratio of the dye including a basic dye and/or an HC dye in the reducing first agent is 0.1 to 10 mass %, from the viewpoint of retaining the color of the dyed hair even when hair straightening is performed immediately after hair dyeing.

Advantageous Effects of Invention

With the method for successively performing hair dyeing and hair straightening according to the present invention, the color of dyed hair can be sufficiently maintained even when hair straightening treatment is performed immediately after hair dyeing.

DESCRIPTION OF EMBODIMENT

An embodiment of a method for successively performing hair dyeing and hair straightening according to the present invention will be described in detail with reference to the drawings.

Figure 1:
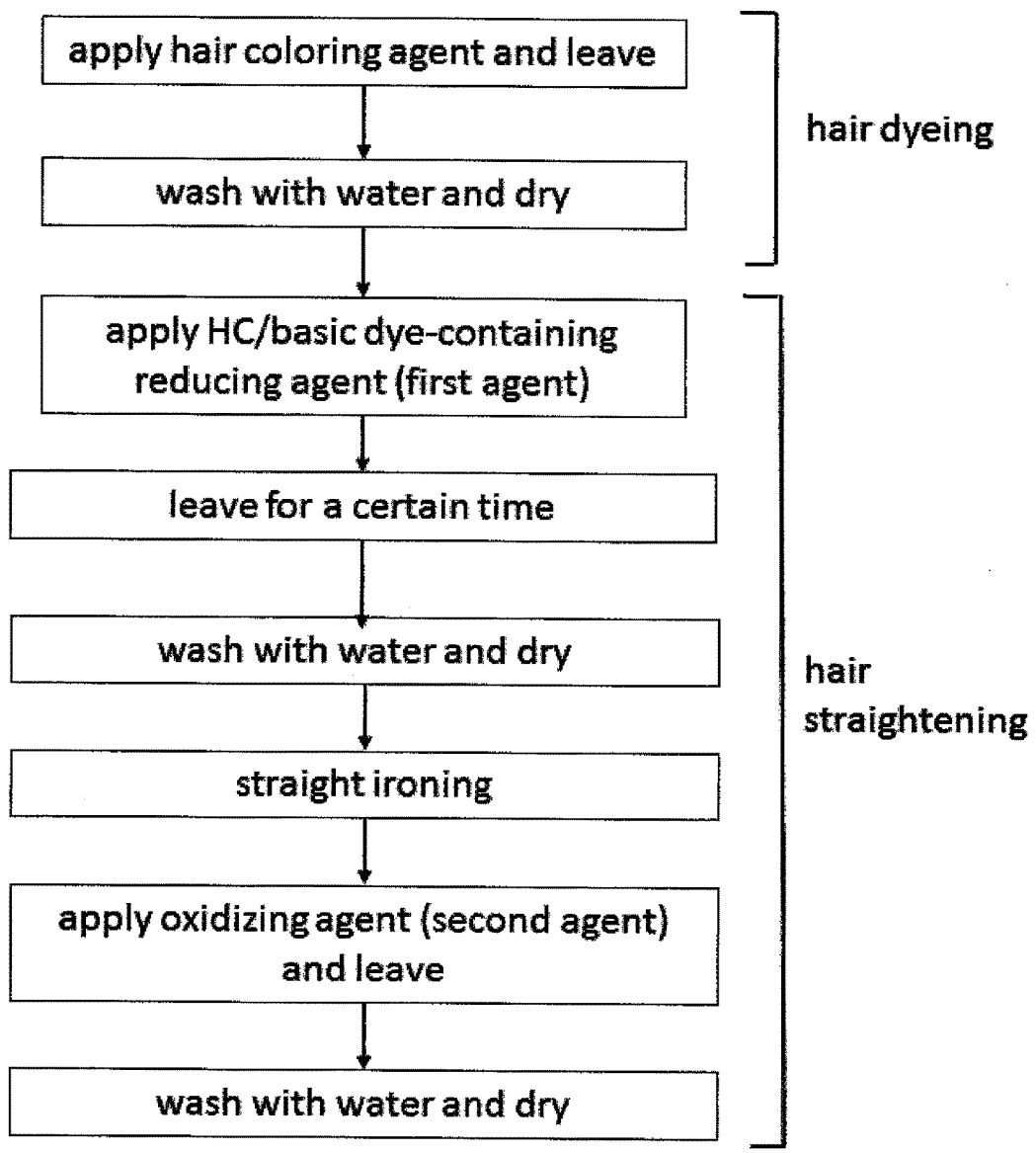
FIG. 1 is a flowchart illustrating the flow of a process of a method for successively performing hair dyeing and hair straightening according to the present embodiment.

FIG. 1 is a flowchart illustrating the flow of a process of a method for successively performing hair dyeing and hair straightening according to the present embodiment. In the successive performing method according to the present embodiment, dyeing (hair coloring) is first performed on the hair of a person to be treated.

The method of dyeing is not particularly limited, and any method conventionally used for dyeing hair may be used without any particular limitation. Specific examples thereof include a hair dyeing method using an oxidation dye, the method involving providing a first agent containing a p-phenylene diamine-type or aminophen-type oxidation dye, which is a commonly used synthetic dye, and an alkaline agent with a second agent containing an oxidizing agent such as a hydrogen peroxide solution, applying, to the hair, a two-agent type hair coloring agent prepared by mixing the first agent with the second agent, and leaving the hair for a certain time, followed by washing with water, and a hair dyeing method using a basic dye and/or an HC dye, the method involving providing a first agent containing a basic dye and/or an HC dye and an alkaline agent and a second agent containing an oxidizing agent such as a hydrogen peroxide solution, applying, to the hair, a two-agent type hair coloring agent prepared by mixing the first agent with the second agent, and leaving the hair for a certain time, followed by washing with water.

The above-described alkaline agent is a component that serves to promote penetration of effective components such as the dye component or the oxidizing agent contained in the second agent by opening the cuticle by swelling the hair, and promote decomposition of melanin by enhancing the oxidation capability of the oxidizing agent. Specific examples of the alkaline agent include ammonia water, ammonium carbonate, sodium carbonate, monoethanolamine, ammonium hydrogencarbonate, and arginine. Among these, ammonia water and ammonia hydrogen carbonate water are particularly preferable. These may be used alone or in a combination of two or more.

The oxidizing agent such as a hydrogen peroxide solution is also called "oxidation agent", and has the function of serving as the bleaching agent for decomposing melanin in hair to achieve enhanced brightness, and the function of promoting the polymerization of an oxidation dye in the case of using the oxidation dye.

After the hair coloring agent as described above is applied to the hair, the hair is left for a certain time, followed by washing with water, optionally shampooing or conditioning, and drying with a hair drier, according to a conventional method. In this way, dyeing is performed.

In the method for successively performing hair dyeing and hair straightening according to the present embodiment, hair straightening treatment is further performed as a series of operations immediately after performing dyeing on the hair of the person to be treated.

As shown in FIG. 1, the process of hair straightening treatment is performed through the following steps. A reducing first agent containing a reducing agent such as thioglycolic acid and a basic dye and/or an HC dye is applied to the dyed hair, and the hair is left for a certain time, thereby to break, to a certain degree, cystine bonds that crosslink the keratin forming the hair structure, and washing with water and drying are performed on the hair. By breaking the cystine bonds to temporarily eliminate the cross-linked structure that causes curly or frizzy hair, the distortion of the hair is reduced. Then, the hair in which the cystine bonds have been broken is subjected to straight ironing or the like so as to shape the hair into a straight configuration. Next, an oxidizing second agent containing an oxidizing agent such as sodium bromate or hydrogen peroxide is applied to the hair that has been shaped into a straight configuration, and the hair is left for a certain time, to reform the cystine bonds with the hair kept shaped in a straight configuration, thereby fixing the straight hair structure. Then, washing with water and drying are performed on the hair according to a conventional method. In the following, each of the steps will be described in detail.

First, a reducing first agent containing a reducing agent and a basic dye and/or an HC dye is applied to the hair that has been subjected to dyeing. The reducing first agent contains mainly a reducing agent and a basic dye and/or an HC dye, and other additives that are optionally blended. Usually, the reducing agent has a pH of about 6 to 8, which is near neutral, and therefore, a basic dye and an HC dye will not cause decomposition or the like that could cause a color tone change when mixed with the reducing agent. In the case of using an oxidation dye, the oxidation dye tends to be decomposed when being mixed with the reducing agent, thus changing the color tone.

Specific examples of the reducing agent include thioglycolates such as ammonium thioglycolate, thiolactic acid, cysteine, cysteamine, acetyl cysteine, thio glycerin, and sulfites.

A basic dye is a dye that has an amino group, a substituted amino group, or the like in the molecule and becomes a cation in an aqueous solution. Those conventionally known as basic dyes may be used without any particular limitation. The basic dye becomes a cation in an aqueous solution, and thus is deposited by being ionically bonded to the anion of the keratin protein on the surface of the hair. Examples of the basic dye include basic red 46, basic red 22, basic red 76, basic orange 1, basic yellow 11, basic yellow 57, basic green 4, basic blue 3, basic blue 99, basic brown 16, basic brown 17, basic violet 2, basic violet 4, and basic violet 14. These may be used alone or in a combination of two or more.

An HC dye is a known dye with the prefix "HC". Specific examples thereof include HC blue 2, HC blue 8, HC orange 1, HC orange 2, HC red 1, HC red 3, HC red 7, HC red 8, HC red 10, HC red 11, HC red 13, HC red 16, HC violet 2, HC yellow 2, HC yellow 5, HC yellow 6, HC yellow 7, HC yellow 9, and HC yellow 12. These may be used alone or in a combination of two or more.

Examples of the other additives that are optionally blended include alkaline agents such as ammonia water, ethanolamine, and an ammonium salt; nonionic surfactants that enhance the permeability of the reducing agent and function as emulsifiers for various components; cationic surfactants for imparting slickness to hair; oily components such as lanolin; NMF (natural moisturizing factor) and other moisturizers; and treatment components composed of protein, polypeptide, which is a hydrolysate thereof, amino acid, or the like.

The concentration of the dye component contained in the reducing first agent is not particularly limited, but is, for example, preferably 0.1 to 10 mass %, more preferably 0.5 to 5 mass %, particularly preferably 0.8 to 3 mass %.

In the hair straightening treatment in the present embodiment, the cystine bonds are broken by the reducing agent by application of the reducing first agent containing the reducing agent and the basic dye and/or the HC dye described above. At this time, the basic dye and/or the HC dye blended in the reducing first agent adheres to the hair surface to inhibit the hair coloring dye from flowing out from gaps in the cuticle that has been loosened by the reducing agent, and also functions as a complementary coloring material for compensating for the color of the hair coloring dye that has flown out.

Figure 2:
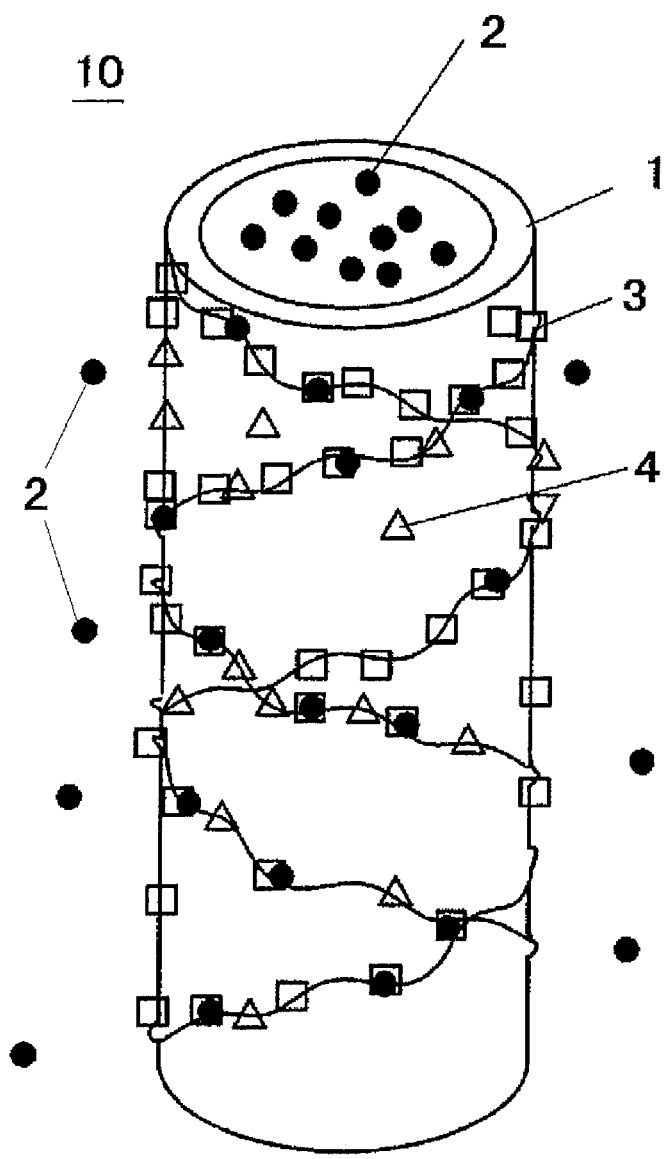
FIG. 2 is a diagram illustrating a function provided by the method for successively performing hair dyeing and hair straightening according to the present embodiment.

FIG. 2 is an diagram schematically illustrating an estimated state when, in the process of the hair straightening treatment, a reducing first agent containing a basic dye 3 and/or an HC dye 4 as described above is applied to hair 10 immediately after the hair 10 has been dyed with a hair coloring dye 2. As shown in FIG. 2, when the reducing first agent is applied in the process of the hair straightening treatment, the cystine bonds are broken to loosen the bonding between keratin molecules, as a result of which the hair coloring dye 2 attached to or charged in the internal matrix covered with the cuticle 1 is about to flow from the gaps in the cuticle 1 to the outside. In such a case, it seems that the basic dye 3 and/or the HC dye 4, having a relatively large molecular weight, fills the gaps to inhibit the hair coloring dye 2 from flowing to the outside.

The hair to which the reducing first agent has been applied is optionally wrapped, and subsequently left for a certain time until it is confirmed to have been reduced to a certain degree, followed by washing with water and blow drying with a hair dryer or the like. Then, straightening with a hair iron or the like is performed on the hair that has been subjected to reduction in this way, thereby to shape the curly or frizzy hair into a straight configuration. As this process, a process similar to processes conventionally used in hair straightening may be used without any particular limitation.

Then, the oxidizing second agent containing an oxidizing agent is applied to the hair that has been shaped into a straight configuration, and the hair is left for a certain time, thereby to reform the cystine bonds.

As the oxidizing second agent, any oxidizing agent that has been conventionally used for hair straightening treatment may be used without any particular limitation. Specific examples of such an oxidizing agent include a hydrogen peroxide solution and bromate. It is usually preferable that the hydrogen peroxide is contained at 2.5% or less and with a pH within the range of 2.5 to 4.5, and it is usually preferable that the bromate is contained at 3.2% or more and with a pH within the range of 4.0 to 9.0.

Then, the oxidizing second agent is applied to the hair, and the hair is left for a certain time, thereby to reform the cystine bonds of the hair structure so as to fix the shape of straight hair. Then, the hair that has been treated in this way is washed with water, thereby to wash off the oxidizing second agent. After washing off, finishing such as shampooing, towel drying, or air drying is optionally performed.

Through these steps, a method for successively performing hair dyeing and hair straightening can be achieved that can retain sufficient color development provided by hair dyeing.

EXAMPLES

Hereinafter, the present invention will be described in further detail by way of examples. It should be appreciated that the scope of the present invention is by no means limited by the examples.

Example 1

With 50 g of a base color dye obtained by mixing a cream base containing cetanol as a main component with 5 mass of a dye mixture obtained by mixing a basic dye and an HC dye serving as dye components at 9:1, 50 g of an alkaline agent containing ammonia water and ammonium hydrogencarbonate was further mixed, to prepare a dye first agent.

Then, 30 g of a 4.5% hydrogen peroxide solution was mixed with 30 g of the first agent, to prepare a hair coloring agent.

Next, the prepared hair coloring agent was applied to the hair of a female subject with brown-dyed hair. Then, the hair to which the hair coloring agent had been applied was left for 10 minutes.

Then, the hair was washed with a commercially available shampoo. Then, the water on the hair was fully wiped off with a towel, followed by drying with a hair drier. In this way, the hair was subjected to cosmetic hair dyeing. At this time, the hair was properly dyed in a dark brown color of Level 8 defined on Hair Coloring Level Scale sold by JAPAN HAIR COLOR ASSOCIATION (JHCA).

Then, a reducing first agent containing a basic dye, an HC dye, and a reducing agent was applied to the hair that had been subjected to cosmetic hair dyeing in the above-described manner, and the hair was left for about 20 minutes, followed by washing with water, and further drying with a hair drier. Note that the reducing first agent used here was prepared with a formulation containing 6 mass % of ammonium thioglycolate, 0.8 mass % of a basic dye (basic brown), 0.2 mass % of HC dyes (HC red, HC blue, HC yellow), 2.4 mass % of ammonia water, and water as the remainder.

Then, the hair that had been subjected to reduction in the above-described manner was stretched with a hair iron so as to be shaped into a straight configuration. Then, the oxidizing second agent was applied to the hair that had been shaped into a straight configuration, and the hair was left for about 10 minutes, followed by washing with water, and further drying with a hair drier. Note that the oxidizing second agent used here was prepared with a formulation in which a 6 mass % hydrogen peroxide solution was adjusted to about 1.5 mass % with water.

In this way, hair dyeing and hair straightening were performed as a series of treatments. The resulting hair retained a dark blown color of Level 8 defined on Hair Coloring Level Scale, which was the same as the color of the hair immediately after dyeing.

Example 2

Instead of performing hair coloring on the hair of the female subject with brown hair by using a basic dye and an HC dye as the dye components in Example 1, hair coloring was performed on the hair of another female subject with brown hair by using a p-phenylenediamine-type oxidation dye as the dye component so as to dye the hair into a dark blown color of Level 8 defined on Hair Coloring Level Scale. Hair dyeing and hair straightening were performed as a series of treatments in the same manner as in Example 1 except that the hair coloring method was changed. The resulting hair retained a dark blown color of Level 8 defined on Hair Coloring Level Scale, which was the same as the color of the hair immediately after dyeing.

Example 3

Hair dyeing and hair straightening were performed as a series of treatments in the same manner as in Example 1, except that the treatments were performed on the hair of another female subject with brown-dyed hair by using a reducing first agent having the following composition and in which only a basic dye component was blended as the dye component, in place of the reducing first agent used for hair straightening of the female subject with brown-dyed hair in Example 1. Note that the reducing first agent used here was prepared with a formulation containing 6 mass % of ammonium thioglycolate, 1 mass % of a basic dye (basic brown), 2.4 mass % of ammonia water, and water as the remainder. The resulting hair retained a dark blown color of Level 8 defined on Hair Coloring Level Scale, which was the same as the color of the hair immediately after dyeing.

Example 4

Hair dyeing and hair straightening were performed as a series of treatments in the same manner as in Example 1, except that the treatments were performed on another female subject with brown-dyed hair by using a reducing first agent having the following composition and in which only an basic dye was blended as the dye component, in place of the reducing first agent used for hair straightening of the female subject with brown hair in Example 1. Note that the reducing first agent used here was prepared with a formulation containing 6 mass % of ammonium thioglycolate, 1 mass % of an HC dye (HC red, HC blue), 2.4 mass % of ammonia water, and water as the remainder. The resulting hair retained a dark blown color of Level 8 defined on Hair Coloring Level Scale, which was the same as the color of the hair immediately after dyeing.

Comparative Example 1

Hair dyeing and hair straightening were performed as a series of treatments on the hair of another female subject with brown-dyed hair in the same manner as in Example 1, except for using a reducing first agent in which no dye component was blended and prepared with a formulation containing 6 mass % of ammonium thioglycolate, 2.4 mass % of ammonia water, and water as the remainder, in place of the reducing first agent containing a basic dye and an HC dye, which was used for hair straightening in Example 1. The resulting hair had a color that was substantially unchanged from the color before dyeing, and substantially no hair dyeing effect was achieved.

Comparative Example 2

Hair dyeing and hair straightening were performed as a series of treatments on the hair of another female subject with brown-dyed hair in the same manner as in Example 1, except for using a reducing first agent in which no dye component was blended and prepared with a formulation containing 6 mass % of ammonium thioglycolate, 2.4 mass % of ammonia water, and water as the remainder, in place of the reducing first agent containing a basic dye and an HC dye, which was used for hair straightening in Example 2. The resulting hair had a color that was substantially unchanged from the color before dyeing, and substantially no hair dyeing effect was achieved.

INDUSTRIAL APPLICABILITY

According to the present invention, it is possible to inhibit the color loss of a hair coloring dye even when hair straightening is performed immediately after hair dyeing, thus enabling hair dyeing and hair straightening to be performed successively. Such successive treatments of hair dyeing and hair straightening can reduce the number of times that a person to be treated needs to visit a hair salon for receiving hair dyeing and hair straightening treatments from twice to once, thus making it possible to save time and trouble for a practitioner and the person to be treated.

The invention claimed is:

1. A method for successively performing hair dyeing and hair straightening, the method comprising the steps of:
   performing dyeing on hair;
   applying, to the hair immediately after being subjected to dyeing, a reducing composition comprising a reducing agent, and at least one selected from the group consisting of a basic dye and an HC dye, and leaving the hair for a certain time, thereby performing reduction on cystine bonds;
   shaping the hair that has been subjected to reduction into a straight configuration; and
   applying an oxidizing agent to the hair that has been shaped into a straight configuration, and leaving the hair for a certain time, thereby performing oxidation for reforming the cystine bonds.

2. The method for successively performing hair dyeing and hair straightening according to claim 1,
   wherein the step of performing dyeing is
   a step of performing dyeing by using a two-agent type hair coloring agent prepared by mixing a dyeing first agent with a dyeing second agent,
   the dyeing first agent includes an oxidation dye and an alkaline agent, and
   the dyeing second agent includes a hydrogen peroxide solution.

3. The method for successively performing hair dyeing and hair straightening according to claim 1,
   wherein the step of performing dyeing is
   a step of performing dyeing by using a two-agent type hair coloring agent prepared by mixing a dyeing first agent with a dyeing second agent,
   the dyeing first agent includes a basic dye and/or an HC dye, and an alkaline agent, and
   the dyeing second agent includes a hydrogen peroxide solution.

4. The method for successively performing hair dyeing and hair straightening according to claim 1,
   wherein a total ratio of the dye including at least one selected from the group consisting of a basic dye and an HC dye in the reducing composition is 0.1 to 10 mass %.

* * * * *